United States Patent [19]

Massau

[11] Patent Number: 4,838,877
[45] Date of Patent: Jun. 13, 1989

[54] POLYMERIC HYPODERMIC DEVICE

[76] Inventor: Bruce A. Massau, 4339 Foxhaven NW., Canton, Ohio 44718

[21] Appl. No.: 944,322

[22] Filed: Dec. 19, 1986

Related U.S. Application Data

[63] Continuation-in-part of Ser. No. 762,821, Aug. 6, 1985, abandoned.

[51] Int. Cl.⁴ ............................................. A61M 5/32
[52] U.S. Cl. .................................... 604/272; 604/264
[58] Field of Search ............................. 604/272–274, 604/95, 264

[56] References Cited

U.S. PATENT DOCUMENTS

| | | | |
|---|---|---|---|
| 2,097,039 | 10/1937 | Peterson | 604/272 |
| 2,954,768 | 10/1960 | Hamilton | 604/274 |
| 3,127,894 | 4/1964 | Smith | 604/274 |
| 3,831,814 | 8/1974 | Butler | 604/274 |
| 4,699,612 | 10/1987 | Hamacher | 604/274 |
| 4,710,180 | 12/1987 | Johnson | 604/27 |

FOREIGN PATENT DOCUMENTS 0174011  3/1986  European Pat. Off. ............ 604/272

*Primary Examiner*—John D. Yasko
*Assistant Examiner*—Mark F. Colosimo
*Attorney, Agent, or Firm*—D. O. Nickey

[57] ABSTRACT

There is disclosed a polymeric hypodermic device that comprises a hollow polymeric needle for injection of substances beneath the skin. The polymeric hypodermic device is constructed of a polymeric material such as polyetheretherketones, polycarbonates, polyetherimides, polymethylpentenes, and other synthetic material having bio-compatibility and possessing sufficient structural strength in such fine structures so as to result in penetration of the skin and adjacent body tissues. The invention provides a novel injection end through which the medication is injected in a direction other than parallel to the axis of the needle, which has had a swirling motion imparted to it, thus lessening trauma to tissue and veins. In addition, said injection end is conical in shape with portals above a solid conical penetrating point, the outer surfaces of the device converge uninterruptedly forward from opposite sides of a tube to a needle sharp point, above said conical penetrating point two or more portals equally spaced along the outside diameter of the device are flush with the exterior of the outer surface of the device and wherein the side walls of the portal are configured so as to impart an angular momentum to the fluid to be injected. Another aspect of this invention is concerned with the use of such a unique polymeric needle for body fluid gathering that lessens the chances of arterial trauma and hemolysis.

5 Claims, 2 Drawing Sheets

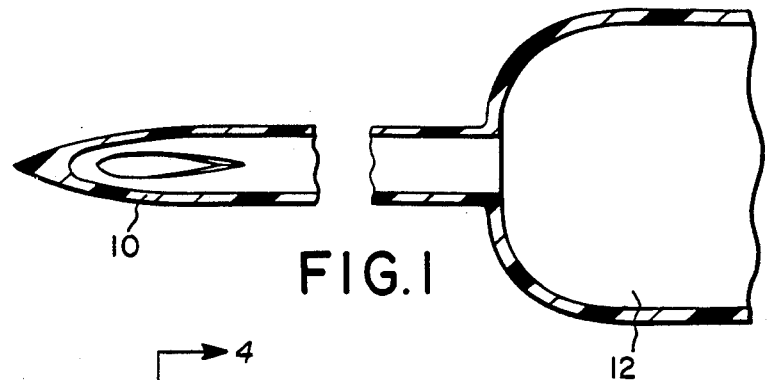
FIG.1
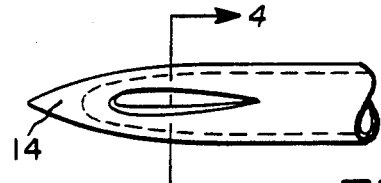
FIG.3
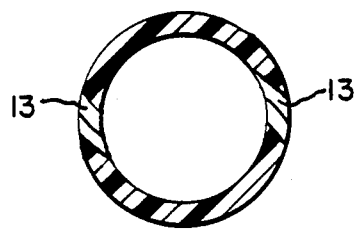
FIG.4
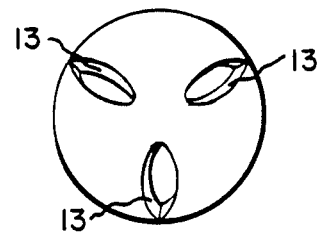
FIG.2
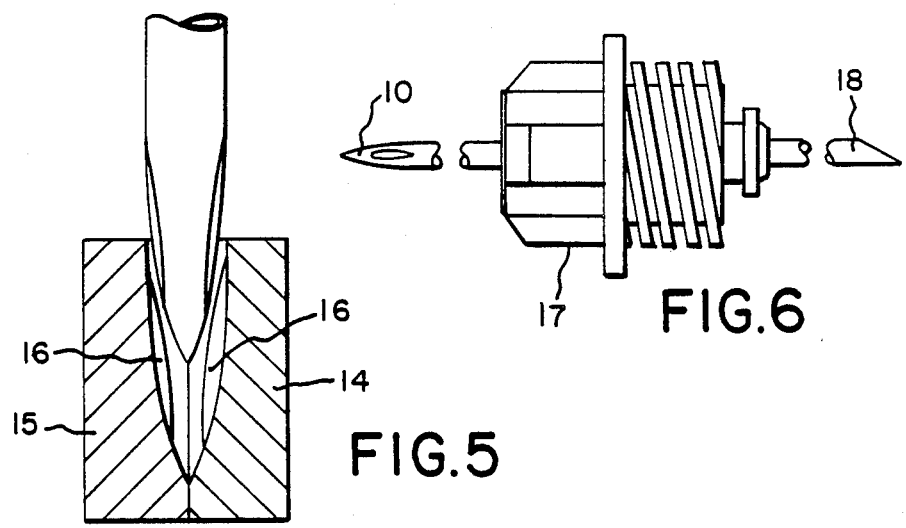
FIG.5
FIG.6

POLYMERIC HYPODERMIC DEVICE

This application is a continuation-in-part of Ser. No. 762,821 filed Aug. 6, 1985, now abandoned.

TECHNICAL FIELD

This invention relates to hypodermic injection devices for performing intradermal, subcutaneous, intravenous, intrathecal, intrauterine, or intramuscular injections for medical or veterinary use. In particular, this invention provides a polymeric needles that possesses an injection end that lessens trauma to surrounding tissue and delivers the substance to be injected in such a manner that causes less discomfort to the patient.

Despite the effectiveness of hypodermic injection devices in general use, certain difficulties and objectionable features still prevail. The available metal devices which are commercially used do not permit early detection of entry into a vein, since it is necessary for the blood to transit the entire length of the steel needle before it is visible to the eye of the physician or technician. It is, therefore, not infrequent that the penetration of the needle, sometimes referred to as a cannula, has been carried through one or more veins without there being any indication of the position of the needle tip at any time. The results of such excessive penetration, coring and trauma are unnecessary hemorrhage at the point of incision as well as an objectionable discoloration, frequently with painful discomfort at the area of injury by the needle.

Other limitations are the brittleness of ferrous needles and the tendency on occasion to break, leaving needle fragments embedded beneath the skin and underlying tissue. Such accidents may be of serious consequence, necessitating resort to surgery for removal of the needle fragments. Other hazards which may occur with hard steel needles that are reduced through this invention are the unintentional and frequently harmful penetration of the peridental membrane or periosteum and bone structure.

A major fault of conventional hypodermic needles is the "coring" of tissue during insertion. This coring is caused by the shape of the needle point which is a biased tube. Another limitation of the presently accepted hypodermic devices is the trauma to muscle tissue caused by the high pressure injection of the fluid due to the shape of the point and the forcing out of the cored tissue. In addition, the high concentration of injected material is detrimental to muscle tissue, and research has determined that necrosis of muscle tissue occurs in the conventional injection device. The present invention, through its multi-ported conical configuration, wherein the side walls of the portal impart a swirling motion, angular momentum or torque to the fluid to be injected overcomes this limitation, and in an intermuscular injection, allows for deposition of the injected substance in a manner that is less damaging to the tissues. In addition, a contemplated aspect of the present invention includes a fluid gathering device having high surface area entry ports. Further, the inherent nature of the polymers utilized provides for lessened drag in the tissue, and thus, causes less discomfort to the patient. The benefits of this invention ultimately result in less discomfort to the patient and ease of use for the operator.

BACKGROUND ART

U.S. Pat. No. 2,512,568 discloses and claims a hypodermic injection device being composed of an organic resinous material, said needle and barrel being integral and having a sharp edge adapted to pierce and penetrate the skin adjacent to the underlying tissue. U.S. Pat. No. 2,512,568 in general describes a polymeric needle, but does not suggest the unique structural configuration of the injection end disclosed herein. The injection end disclosed in U.S. Pat. No. 2,512,568 is the same biased end that is used today in metal needles. U.S. Pat. No. 2,512,568 is herein incorporated by reference.

U.S. Pat. No. 4,369,768 discloses and claims a fiber optics device, or operative arthroscope, wherein a fiber optic channel containing a number of fiber optic strands are secured and retained in place through a sleeve which may be plastic or metal. The flexible sheath encases the entire operative assembly carrying the irrigation channels. There is no suggestion that the polymeric portion of the device could be used to penetrate the skin. In fact, the use of the '768 device requires a surgical procedure prior to entering the body.

U.S. Pat. No. 3,940,802 is concerned with a medical appliance made of plastic, more specifically, polyvinylchloride wherein the polyvinylchloride is made more suitable for us in direct or indirect contact with human blood via the use of a polyurethane as a plasticizer.

U.S. Pat. No. 2,954,768 discloses a puncture point comprising a tubular shaft; an inner surface on said shaft defining a longitudinal passage: a conical point: a frustoconical shoulder between said shaft and said point: walls defining channels extending longitudinally through said shoulder and along a portion of the shaft. In addition, this patent describes a device that possesses walls that slant inwardly toward the bottom of each channel which meet the inner surface of the shaft thereby defining a slot in each channel opening into the passage and a slanted surface extending rearwardly from each slot to the outer surface of the shaft. The injection or puncture device of U.S. Pat. No. 2,954,768 contains walls defining channels extending longitudinally through a shoulder which are not present in the instant invention.

U.S. Pat. No. 3,090,384 discloses a standard bias cut tube wherein the main bevel of the lancet extends at a 12 degree angle with reference to the needle axis and side bevels extended at 15 degrees with reference to the needle axis. This patent does not suggest a solid conical penetrating point with an included angle of from 10–22 degrees nor does it suggest the exit portals of the instant invention which possess side walls that are cut so as to impart a swirling motion or torque to the injected fluid.

U.S. Pat. No. 3,645,268 is concerned with a self locating and piercing evacuator tube. This ear evacuator possesses a shoulder and cutting edges for incision of the tympanic membrane. The instant invention does not possess cutting edges, nor the shoulders or stop means of the '268 device.

Germany DE No. 3020926 discloses a syringe for lumbar puncture which has a conical closed needle tip with lateral aperture. This reference fails to disclose or suggest portals flush with the exterior of the device which would impart angular momentum to the injected fluid. Further, this German reference contains a singular portal that is ground into the tube which adds additional surfaces to the exterior of the device and thus would not be flush with the exterior of the device. In addition, the referenced device would not spiral or impart an angular momentum to the injected fluid as would the instant invention.

U.S. Pat. No. 4,411,661 discloses a spike connector having a main body portion and a hollowed spike extending therefrom for insertion into the stopper of a fluid source, the improvement comprising a pair of wings extending from the spike. This device designed to drain fluid from a container possesses openings or portals that are not flush with the exterior surface and further if used to inject a fluid would not do so in a swirling motion. In addition, the device possesses a shoulder at the junction of the conical point and the shaft of the tube which is not an aspect of the instant invention.

U.S. Pat. No. 4,413,993 discloses an infiltration proof intravenous needle comprising a round elongated hollow needle shaft tapering to a completely round elongated tip terminating in a sharp point lying on the axis of the needle shaft and an opening of said needle shaft. This patent fails to disclose the essential feature of the instant invention, that being the configuration of the opening or portal which would impart torque or angular momentum to the fluid to be injected. This patent fails to appreciate the beneficial effects that can be realized when the fluid is injected in a swirling motion. That motion or angular momentum is accomplished in this invention through the design of the walls of the opening or portal.

One common shortfall of the presently accepted hypodermic injection devices is that the substance to be injected is done so in a manner parallel with the axis of the needle, and thus, causes additional trauma to the surrounding tissue. Related to this effect, is the trauma to tissue caused by high pressures that are generated by the injection of both the medication and the forcing out of the tissue which was cored when the skin and subcutaneous tissues were passed through. In addition, the high concentration of injected material at the site of penetration is detrimental to muscle tissue. The present invention overcomes these problems through a unique configuration of the injection end that provides for delivery of the substance to be injected multi-directionally and substantially perpendicular to the axis of the device in a swirling motion. Through molding or forming techniques of the portal side walls, the torque or swirling of the fluid being injected can be varied as desired. Such a design allows the injection to take place essentially parallel to the muscle fibers and tissue planes. This permits a more natural separation of tissue and consequently less trauma.

Venipuncture is one of the more commonly performed medical procedures. Such surgical puncture of a vein to either withdraw fluid or insert a needle, to administer intravenous fluid can be a difficult and painful procedure for many patients, especially for children or the frequently hospitalized patients in whom it can be difficult to insert a large bore needle into a vein. The present invention minimizes the discomfort associated with such procedures, and is particularly useful in treating children and patients in whom it is hard to find a moderate size vein. Through the ported conical configuration, smaller bore or gauge needles can be used to accomplish what once required a large bore needle.

When an injection is administered to a patient, the tissue around the injection site undergoes a localized area of necrosis or tissue death. In the conventional bias cut ferrous needle, the cored out tissue that is injected in advance of the injectate must displace the surrounding tissue so as to allow the tissue to expand and create a "pocket" for the medication. This causes the stretching of nerve fibers in the muscle and produces the sensation of pain. The injected medication displaces the surrounding tissue in a manner that is perpendicular to the muscle fibers; thus causing pain.

The site of skin penetration and associated trauma to this area requires time to heal. The conventional ferrous needle with its coring effect requires a longer healing process. A close examination of the wound from a conventional needle will exhibit a cut, similar to the one that is created by a surgical incision. The needle of this invention does not produce an incision but a puncture. The puncture site will heal more quickly than will a cut surface. In addition, the inherent nature of the various polymers utilized in the needle construction will eliminate tissue drag almost entirely. This would cause less "pulling of the tissue" thus less discomfort to the patient.

None of the prior art suggests or discloses the instant device which overcomes the numerous problems presently tolerated in the medical profession.

DISCLOSURE OF THE INVENTION

There is disclosed an injection device comprising an injection end and constructed of a polymeric material, said injection end is of a ported configuration that delivers the material to be injected in a direction other than parallel with the axis of the device and said injection end is conical in shape with portals above a solid conical penetrating point:

the improvement comprising the outer surfaces of the device converging uninterruptedly forward from opposite sides of a tube to a needle sharp point wherein two or more portals equally spaced along the outside diameter of the device are flush with the exterior of the outer surface of the device and wherein the side walls of the portal are configured so as to impart an angular momentum or torque to the fluid to be injected.

The invention additionally contemplates a hypodermic syringe wherein the needle and barrel or ampule portions are integral with each other. Such a needle and ampule, in combination with the ported-conical injection end, would possess the unique feature of injecting the fluid essentially parallel to the muscle fibers without coring of the tissue.

Another contemplated application of this polymeric device will be in the area of blood and fluid collection from the body. Currently, when a conventional needle is inserted into a vein for blood sampling, a special negative pressured collection tube is utilized to create a vacuum in which the blood is literally suctioned from the vein and into the collection tube. This leads, in some cases, to destruction of some of the blood cells which will then produce errors in the values of laboratory analysis. This can seriously affect medial intervention.

As described, the location of the multiple ports also facilitates blood collection. The opening parallel to the blood flow allows them to act as "large storm sewers" for the collection of fluids or the administration of medication. This more natural flow decreases damage to the blood elements. The vein is punctured and not cut as commonly found in the conventional needle.

The invention will be further defined and its advantages and features will become apparent from the following description read in connection with the accompanying drawings.

DESCRIPTION OF THE FIGURES

FIG. 1 relates to an enlarged longitudinal sectional view, partially broken, of a syringe, the barrel and tubular needle being integrally formed, the needle possessing the unique ported-conical injection end.

FIG. 2 is directed to an end view of the injection device. The number of ports may be more or less than the three depicted. As depicted, the portals are flush with the exterior of the device.

FIG. 3 relates to a side view of the injection device with line 4—4.

FIG. 4 is the cross section through FIG. 3 at line 4—4 which relates to the shape of the portals wherein the side walls of the portal are configured so as to impart an angular momentum or torque to the injected fluid. Reference numeral 13 is a portal which possesses side walls that have leading and following faces that are angled or slanted so that a torque is applied to the injectate that results in the swirling motion of the fluid.

FIG. 5 relates to a sectional view of a two-part mold that upon closure will form the novel injection end of this invention. The reference numerals 16 represent the cutting blades which will produce side walls that will impart an angular momentum to the fluid.

FIG. 6 relates to a blood gathering needle having the customary collar, customary needle end and the novel end of this invention. This device is unitary in construction.

Figure 7:
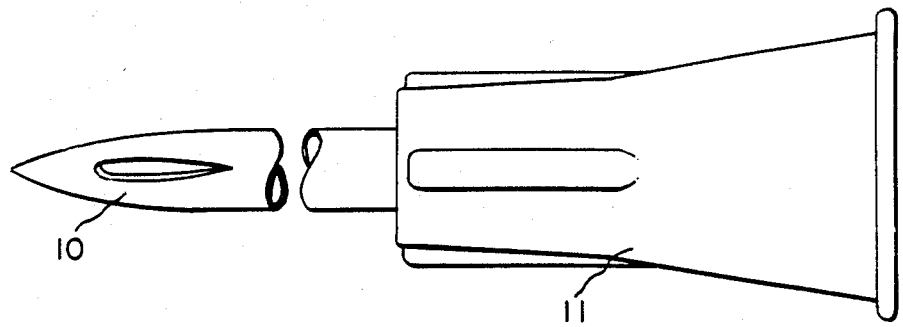
FIG. 7 relates to a unitary construction possessing the novel end and a Luer adaptor.

Referring more particularly to the features in FIG. 7, the hollow fluid-transmitting needle is of a unitary construction and comprises the novel injection end of this invention 10 and a conventional end or Luer hub 11 for insertion onto a capsule or ampule that contains the fluid to be injected. The collar 11 is for anchoring the needle to the syringe or injection device. The needle and collar combination is of one-piece transparent or translucent material.

With reference to FIG. 1, the needle with novel end 10 and ampule 12 are of one material and one part, and the production of the needle and annual is made in accordance with the known practices in the art of molding, such as molding by extrusion or casting.

With reference to FIG. 4, the cross section through 4—4, illustrates the ports 13 that are configured so as to impart an angular momentum to the fluid being injected, that is the fluid injected exits at a direction other than parallel with the axis of the needle and in a spiral manner. The ports 13 are cut with blades 16 from FIG. 5 or are cut with the use of a laser. The most important aspect of these portals whether tear drop in shape, rectangular, and so on is that the walls or faces be configured so as to produce the swirling motion. The curvature or angles of these walls are not unlike the blades of a turbine or centrifugal pump.

The injection device of this invention possesses a ported conical end 14 like the taper point of a common needle, it enters the patient via blunt dilatation with no cutting action whatsoever. When the hole is fully developed, the rest of the shaft slides through with friction as the major resistance. With the conical or taper point 14, the included angle (at the apex of the cone) can range from approximately 10°-22°. When the needle's included angle is more acute, less work per unit time would re required to make a fully developed hole. However, the more acute the angle, the more fragile the tip, with resultant possible failure. When the angle is much greater than 20°, the dilatation per unit time must be faster and the needle appears to be more blunt because of the necessity for rapid dilatation.

As depicted in FIG. 2, the portals are flush with the exterior of the device. This means that the instant device does not possess any channels, shoulders or other surfaces that interrupt the converging forward of the outer surface of the device to a needle sharp point. Many of the prior art devices possess channels or shoulders which would increase the discomfort experienced since these additional surfaces or features would cause tearing or compression of the skin.

With reference to FIG. 2, the end view depicts three exit portals 13 that will provide for injection of the fluid in a swirling manner. The number of portals may range from 2 to 4 with 3 being preferred. With reference to FIG. 5, the two parts of the mold 15 and 14 close on the preformed tube or needle to cut or form the exit portals. The cutting blades 16 are sharp and may be heated to above the melting point of the polymer. The cutting blades in this embodiment are triangular in cross section with different angles for each of the two surfaces with respect to a line from the apex of the triangle to the base of the triangle, said line is perpendicular to the base of the triangle. These different angles are such that an angular momentum or torque is applied to the injectate.

With reference to FIG. 6, the novel end 10 is in combination with a conventional collar 17 and the prior art needle end 18. This device is unitary in construction and has utility in the gathering of fluids from a patient.

Representative of the polymeric materials which can be used to construct the instant invention are the polycarbonates, polyesters, acrylates, polyaramides, polyamides, polyetheretherketones, modified phenylene oxides, polyetherimides, polymethylpentenes, polysulfones, and other know polymeric materials that are transparent, have compatibility with living tissue and the structural integrity required to penetrate living tissue.

The medical appliance of the subject invention is made of polymeric materials which meet the non-toxicity requirements specified by the appropriate governmental authorities. Polymeric materials are known to meet such requirements and possess the required stiffness for penetration, transparency, and yet process with ease.

BEST MODE OF THE INVENTION

Numerous procedures can be used to form the novel injection end of this invention, such as injection molding, thermoforming and machining. One preferred procedure involves the extruding or drawing of a tube to the desired size. For example a Lucite ™ tube with an outside diameter of ¼" with an inside diameter of ⅛" and a wall thickness of 1/16" was heated to about the glass transition temperature of Lucite ™. The tube in a vertical direction was pulled or drawn to a gauge of approximately 18 through the use of a pulling or drawing action. This drawing or pulling of the tube narrows its dimensions and is done in such a manner so as to result in a tube of the required size for use as a hypodermic device. The temperature at which the drawing can be conducted is at or about the glass transition temperature of the polymer. Those skilled in the art of polymers will appreciate that each polymer, such as polyester, polycarbonate, acrylic, etc., will have an appropriate temperature at which this drawing can be conducted.

Those skilled in the art of drawing fibers, such as polyester fibers, will appreciate the drawing rates and initial tubular dimensions required to result in a tube of the appropriate size for use as a hypodermic device. This fine tube is then placed in a two-section mold that upon closing places the injection end and ports on the tube. The mold is segmented and contains protrusions that on closing of the mold forms the ports as depicted in FIG. 5.

These protrusions are triangular in cross section with angles relative to the base of the triangle that are different for each surface. Those skilled in the art of fluid mechanics will appreciate what angles will be required to achieve the side wall configuration of the portal so as to provide a torque or angular momentum to the injectate. The exit portal side walls create a torque upon the exiting fluid. This torque gives rise to the production of a flow which has a two vector direction. Preferably, the leading and following faces of the portal side walls are at different angles so as to impart the torque.

The rate of dissipation of energy in a fluid depends only on the viscosity of the fluid and on the instantaneous distribution of that velocity. Since velocity is a function of pressure, the rate of dissipation of energy can be altered by the design of the exit port. Thus, the dispersal created by the two exit vectors will dissipate the energy in an uniform manner and, therefore, the pressure needed to mobilize the fluid will be minimal as compared to an open end system such as the conventional bias cut tube.

The key of the instant invention resides in the torque or angular momentum imparted on the exiting fluid which readily dissipates the energy. Thus, the instant invention will provide an injection made with less force and thus less tissue damage.

The shape of the exit portal side walls will create the circular flow with a small loss of energy in the form of turbulence which is less than the energy lost to turbulence in an open end system.

Another preferred procedure to form the novel injection end of the instant invention is to injection mold the needle shape, and then using a laser, burn or cut the polymer to form the ports. Preferably, the laser would cut one wall of the port at an appropriate angle and then the opposite wall or face at a different angle so that the fluid would have a torque applied to it. Those angles can be varied and are readily ascertainable by one knowledgeable in turbine and centrifugal pump design.

In addition, the novel injection device can be produced via technologies such as injection molding, cutting with drills and/or knives, cutting with lasers, extrusion and the like.

The exterior dimensions of the device of this invention are those that are customary in the art. Preferably, 18 gauge to 25 gauge needles are contemplated The area of the portals is preferably the maximum that can be obtained with the process of manufacture and the polymer utilized.

The device of the instant invention can also be produced through extrusion. As in conventional polymer technology, the material is heated and then forced through a die at an appropriate speed and pressure. This extruded tube may then be drawn or pulled to achieve the appropriate size for a hypodermic device.

In the extrusion process, the polymer is initially heated in an extruder or a similar installation equipped with a heating and mixing device, to or above its melting or softening point, the extruded tube is partially cooled below the melting point, optionally drawn to a finer structure, and subsequently in an accessory installation submitted to further processing to place the novel end on the device via a forming device, compression molding or another accessory installation. A structure forming process is described in DE-OS No. 2856580, which is herein incorporated by reference.

The extrusion conditions depend upon the individual polymer used, the amount of optionally present processing aids, the amount of additives optionally employed and of fillers, for example calcium carbonate, glass fibers, short fibers and the like.

After formation of the tube via any appropriate technology, the tube is cut at an angle perpendicular to the axis of the tube. This cut end is then inserted into a heated mold of FIG. 5 that will provide the injection end which is described herein. Two molds may be used in that the first would place the point on the needle, and the second would cut or shape the portals for the needle.

One preferred method of producing the device of this invention is injection molding. The molds themselves should be carefully gated and have an overflow area because it is extremely difficult to fill the mold with "just enough" material. Presently available equipment using highly sophisticated process control devices on small single or multi-cavity molds will result in the best possible hypodermic device. The mold steel or other metal should be neutralized by commercial chemicals and then coated to prevent degradation of the metal. Stainless steel like 440SS, 420SS or others are suggested. The mold should be cleaned before the next molding so as to prevent contamination of the next device to be molded.

Typically, a molding machine of one or two ounce capacity with a general purpose screw design is useful in making the device. It is suggested that the recommendations of the polymer supplier be followed as to set-up of the molding machine.

The manner of injection molding the respective portions of the device within the purview of this invention is subject to a diversification of procedures within the preference and skill of one versed in the molding art. The device may be molded from crosslinked polymer or from an intermediate stage polymer and the article subsequently polymerized to the final stage.

The fabricated devices may be sterilized with ethylene-oxide, steam sterilization, gamma irradiation, or other known techniques.

The shape of the sidewalls of the ports or portals are such that the fluid to be injected exits with an angular momentum or swirling motion. These ports may be square, rectangular, circular, oval, teardrop or fluted in shape but all have the characteristic feature of the slanted or angled side walls as depicted in FIG. 4. The preferred shape is fluted in that not only does the fluid to be injected exit the ports in a direction other than parallel to the axis of the needle, but also in a spiral or circular manner, thus lessening the chances of tissue damage.

This fluted port is formed so that the exiting fluid has an angular momentum imparted to it. This fluted port can be formed through the use of a mold that cuts or forms the fluted port, through injection molding of the device or through cutting the ports with a laser.

Polymers and additives which meet the criteria of bio-compatibility are too numerous to mention, as the state of polymer technology has advanced to a high degree. Useful polymers are those mentioned above. These polymers are compounded to yield translucent or transparent materials in order to permit observation of the prevailing conditions in the needle.

While steel needles of the prior art present a problem in obtaining appropriate sharpness and require special tools and stones to attain satisfactory penetrating characteristics, the polymeric needle of the present invention lends itself to a fine conical point. A further advantage of the present invention over the prior art is that presently accepted steel needles due to their configuration "core" or remove tissue as part of penetration. The device of this invention through its unique injection end lessens or eliminates the coring of tissue. In fact, the instant device is more like a solid steel pin, in that no tissue is cored: only a puncture would results from its use. In addition, polymers have less drag in tissue than steel, thus, further lessening trauma to the surrounding tissue.

In addition to the enhanced effectiveness and adaptability of the hypodermic injection devices within the scope of the invention, the structural simplicity and economy involved are also apparent to those familiar with the production of needles.

One embodiment of the invention is the novel injection end being part of a unitary needle and barrel. As in FIG. 1, through proper molding, injection and drawing technologies or combinations thereof, a simple, sturdy, minimum weight, economical and practical hypodermic injection syringe, in the form of an integral or single unitary member, is provided which can be preloaded with the medication to be injected, i.e., insulin. This and the other embodiments of the invention allow for sterile packaging that is known in the art and then the efficient destruction of the device after its use. The destruction is most effective either through mechanical damage or exposure to temperatures above the glass transition temperature of the polymer. Thus, envisioned is a device as described herein, that is filled at an appropriate laboratory under controlled conditions of sterility, shipped and then distributed. Sterile conditions are maintained through the use of sheaths or covers as known in the medical profession. Following use, the device may be destroyed or discarded.

It should thus be appreciated that the invention is predicated on a novel type of hypodermic injection device or syringe that possesses a structurally novel type of injection end. The use of a polymeric material in combination with a "non-coring" or ported configuration for a hypodermic device overcomes numerous disadvantages presently tolerated by the medical profession and patients alike.

While the details of the disclosure and the drawings are directed to specific embodiments of the invention, it should be understood that these showings are primarily illustrative in scope and are not to be taken by way of restriction or limitation. Thus, the invention will include all embodiments falling within the scope of the claims.

I claim:

1. An injection device comprising an injection end and constructed of a polymeric material, said injection end is of a ported configuration that delivers the material to be injected in a direction other than parallel with the axis of the device and said injection end is conical in shape with portals above a solid conical penetrating point:
    the improvement comprising the outer surfaces of the device converging uninterruptedly forward from opposite sides of a tube to a needle sharp point wherein two or more portals equally spaced along the outside diameter of the device are flush with the exterior of the outer surface of the device and wherein the longitudinal side walls of the portal are configured at difference angles so as to impart an angular momentum or torque to the fluid to be injected.

2. The hypodermic injection device of claim 1 wherein the polymeric material is selected from the group consisting of: -polycarbonates, polyesters, acrylates, polyaramides, polyamides, polyetheretherketones, modified phenylene oxides, polyetherimides, polymethylpentenes and polysulfones.

3. The hypodermic injection device of claim 1 wherein the conical penetrating point has an included angle of 10°-22°.

4. The hypodermic injection device of claim 1 wherein the conical penetrating point has an included angle of 12°-18°.

5. The hypodermic injection device of claim 1 wherein the portals are circular in shape.

* * * * *